United States Patent [19]
Olson et al.

[11] Patent Number: 6,125,298
[45] Date of Patent: Sep. 26, 2000

[54] DEFIBRILLATION SYSTEM FOR PEDIATRIC PATIENTS

[75] Inventors: Kenneth F. Olson, Edina; Byron L. Gilman, Minnetonka, both of Minn.

[73] Assignee: SurVivaLink Corporation, Minneapolis, Minn.

[21] Appl. No.: 09/295,980

[22] Filed: Apr. 21, 1999

Related U.S. Application Data

[60] Provisional application No. 60/092,076, Jul. 8, 1998.
[51] Int. Cl.[7] .................................................. A61N 1/39
[52] U.S. Cl. ............................................................. 607/5
[58] Field of Search ................................. 607/63, 5, 28

[56] References Cited

U.S. PATENT DOCUMENTS

| | | | |
|---|---|---|---|
| 5,441,520 | 8/1995 | Olsen et al. | 607/5 |
| 5,531,769 | 7/1996 | Fossan et al. | 607/5 |

OTHER PUBLICATIONS

Atkins, Dianne L., M.D., *Accurate Recognition and Effective Treatment of Ventricular Fibrillation by Automated External Defibrillations in Adolescents*, Pediatrics, vol. 101, No. 3, Mar. 1998.

*Primary Examiner*—Scott M. Getzow
*Attorney, Agent, or Firm*—Patterson, Thuente & Skaar, P.A.

[57] ABSTRACT

An automatic external defibrillator (AED) includes a device for scaling the stored energy communicated to the patient responsive to a known patient weight. An electrode set, for use with an automatic external defibrillator (AED), the AED includes a plurality of electrodes for making electrical contact with a skin surface of a patient. Each electrode of the plurality of electrodes is electrically connectable to a electrical connector for communicating a stored energy to a patient. The electrodes system further includes a device for scaling the stored energy communicated to the patient responsive to a known patient weight. A method of defibrillating the heart of a human patient using an AED includes the steps of:

adherably placing at least two electrodes on the skin surface of the patient, the electrodes being spaced apart to define a desired energy path therebetween;

scaling the dischargeable defibrillating energy responsive to a known patient body weight; and discharging defibrillating energy across the energy path, the discharge generating an energy vector, the vector being passable through the heart of the patient.

36 Claims, 9 Drawing Sheets

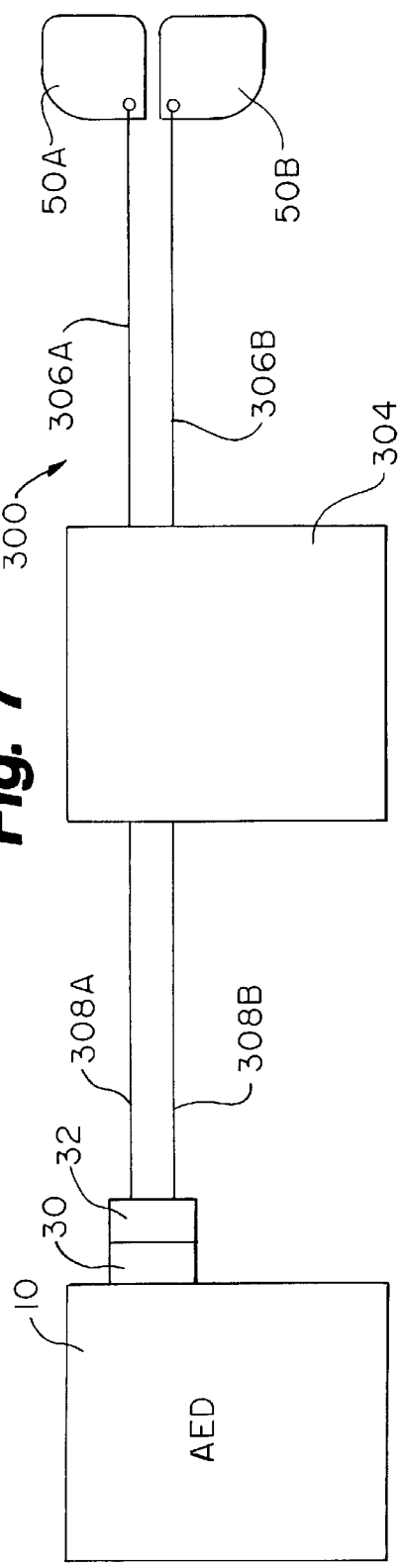
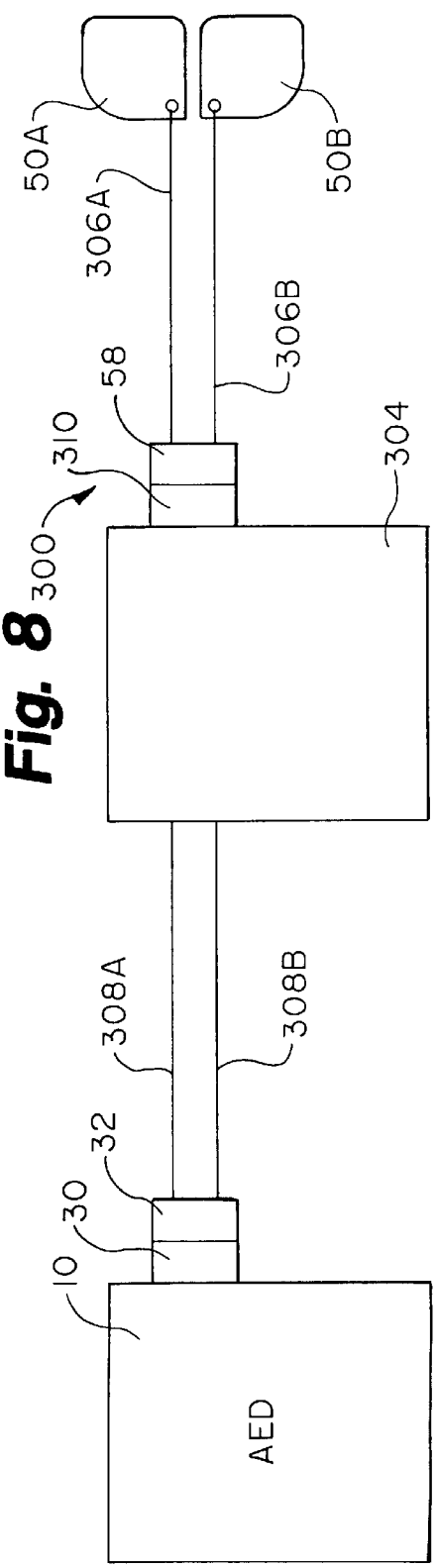

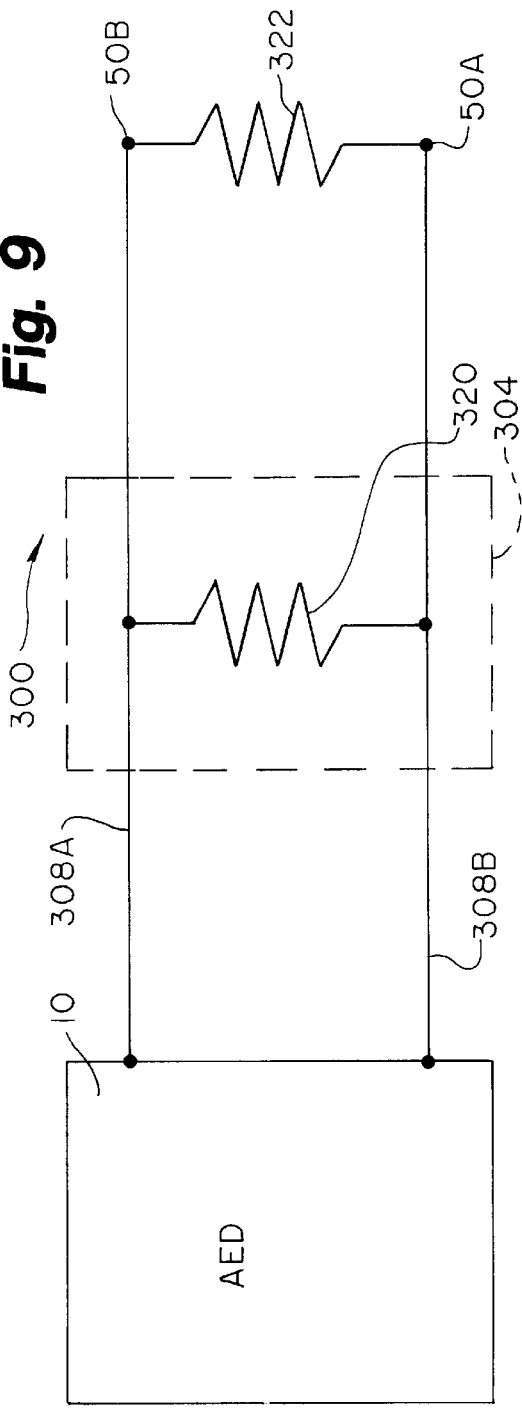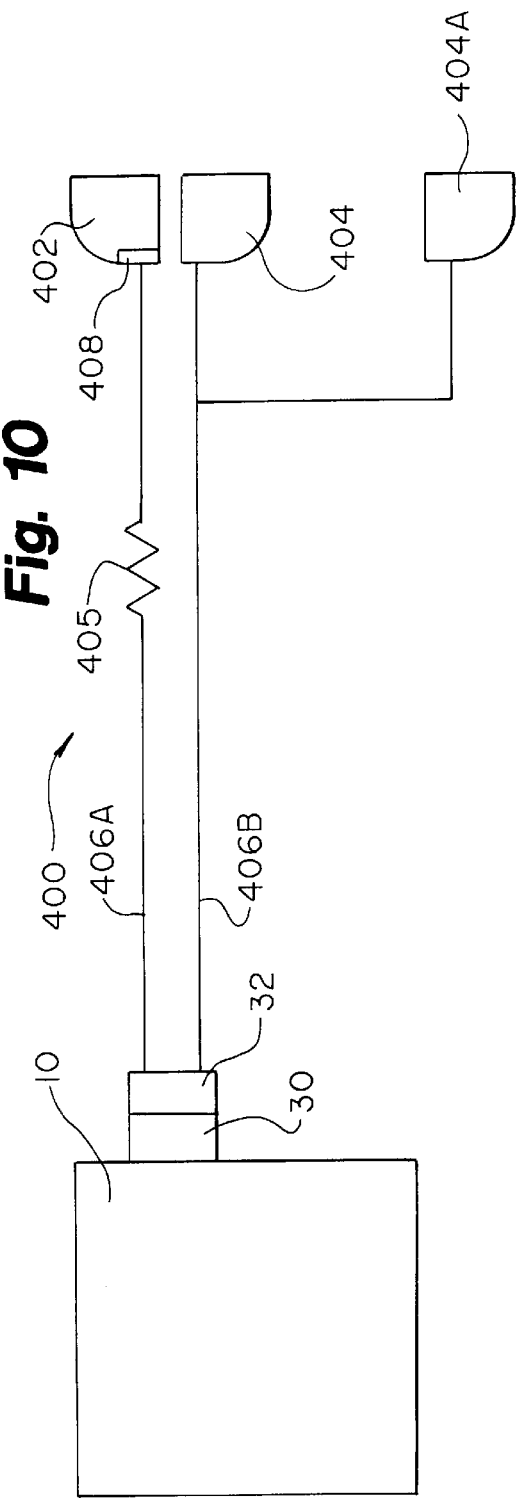

DEFIBRILLATION SYSTEM FOR PEDIATRIC PATIENTS

RELATED APPLICATIONS

The present application claims the benefit of U.S. Provisional Patent Application No. 60/092,076, filed Jul. 8, 1998, incorporated herein by reference.

FIELD OF THE INVENTION

The present invention relates generally to electrotherapy methods and apparatus for delivering an electrical pulse to a patient's heart. More particularly the present invention relates to automatic external defibrillators (AEDs).

BACKGROUND OF THE INVENTION

Cardiac-arrest, exposure to high voltage power lines, and other trauma to the body can result in ventricular fibrillation. Ventricular fibrillation is the rapid and uncoordinated contraction of the myocardium of the heart. The use of external defibrillators to restore the heart beat to its normal pace through the application of an electrical shock is a well recognized and important tool in resuscitating patients. External defibrillation is typically used in emergency settings in which the patient is unconscious.

Automatic External Defibrillators (AEDs) are used by first responders such as police officers, fire fighters, and emergency medical technicians to resuscitate victims of sudden cardiac arrest. Studies have shown that the chances of successfully resuscitating a patient decrease approximately ten percent per minute following the onset of sudden cardiac arrest. Accordingly, a victim of sudden cardiac arrest will most likely not survive unless a trained rescuer responds in less than ten minutes after the cardiac arrest occurs and successfully defibrillates the heart.

Automatic External Defibrillators are designed to be very easy to use so that rescuers without extensive medical backgrounds can successfully resuscitate victims of sudden cardiac arrest. AEDs are currently being carried in emergency vehicles such as police cars, paramedic vehicles, and fire trucks. AEDs are also being widely deployed in areas where large numbers of people gather, such as at sports stadiums, gambling casinos, etc.

In one study, AEDs were used to assess cardiac rhythm in 18 patients with a mean age of 12.1±3.7 years. The cardiac rhythms were analyzed 67 times and included ventricular fibrillation (25), asystole/pulseless electrical activity (32), sinus bradycardia (6), and sinus tachycardia (4). The AEDs recognized all nonshockable rhythms accurately and advised no shock. Ventricular fibrillation was recognized accurately in 22 (88%) of 25 episodes and advised or administered a shock 22 times. Sensitivity and specificity for accurate rhythm analysis were 88% and 100%, respectively. One patient with a nonshockable rhythm survived, whereas 3 of 9 patients with ventricular fibrillation survived.

The data from this study furnish evidence that AEDs provide accurate rhythm detection and shock delivery to children and young adolescents. AED use is potentially as effective for children as it is for adults.

Accordingly, there is a need in the industry for AEDs adapted to deliver therapy to pediatric patients. Preferably, such adaptation should not require extensive modification to existing AEDs.

SUMMARY OF THE INVENTION

The device of the present invention substantially meets the aforementioned needs of the industry by readily adapting existing AEDs that are designed to deliver therapy to adult proportioned persons to smaller individuals. This adapting is accomplished without significant modification of the existing AEDs. In an embodiment, an energy reducer is electrically connected to at least two electrodes such that a portion of an adult-sized energy charge delivered to the electrodes for delivery to a patient is shunted from the electrodes. A lesser, scaled down energy charge appropriate to a pediatric patient is then delivered to the patient.

In another embodiment of this invention, coding of pediatric electrodes is provided to enable the AED to detect and identify a pediatric electrode. This is done by resistance or inductance coding, an imbedded memory chip or other comparable device. A further benefit of certain types of coding, such as inductance coding, is that it allows retrofitting of an AED to be converted to this type of pediatric mode having a scaled down energy charge with no hardware modifications by including a software change and utilization of the specialized pediatric electrodes. A further aspect of this invention is that the electrodes may be further distinguished to allow for a range of ages of body weights which would allow the AED to fine tune the algorithm and to scale the energy dosage to narrower pediatric weight/age ranges.

The present invention is an automatic external defibrillator (AED), including a device for scaling the stored energy communicated to the patient responsive to a known patient weight. The present invention is further an electrode system, for use with an automatic external defibrillator (AED), the AED includes a plurality of electrodes for making electrical contact with a skin surface of a patient. Each electrode of the plurality of electrodes is electrically connectable to a electrical connector for communicating a stored energy to a patient. The electrode system further includes a device for scaling the stored energy communicated to the patient responsive to a known patient weight. The present invention is additionally a method of defibrillating the heart of a human patient using an AED includes the steps of:

adherably placing at least two electrodes on the skin surface of the patient, the electrodes being spaced apart to define a desired energy path therebetween;

scaling the dischargeable defibrillating energy responsive to a known patient body weight; and discharging defibrillating energy across the energy path, the discharge generating an energy vector, the vector being passable through the heart of the patient.

BRIEF DESCRIPTION OF THE DRAWINGS

FIG. 7 is a block diagram of an embodiment of the defibrillation system;

FIG. 8 is a block diagram of a second embodiment of the defibrillation system; and FIG. 9 is a schematic circuit diagram of an embodiment of the defibrillation system.

DETAILED DESCRIPTION OF THE PREFERRED EMBODIMENTS

Figure 1:
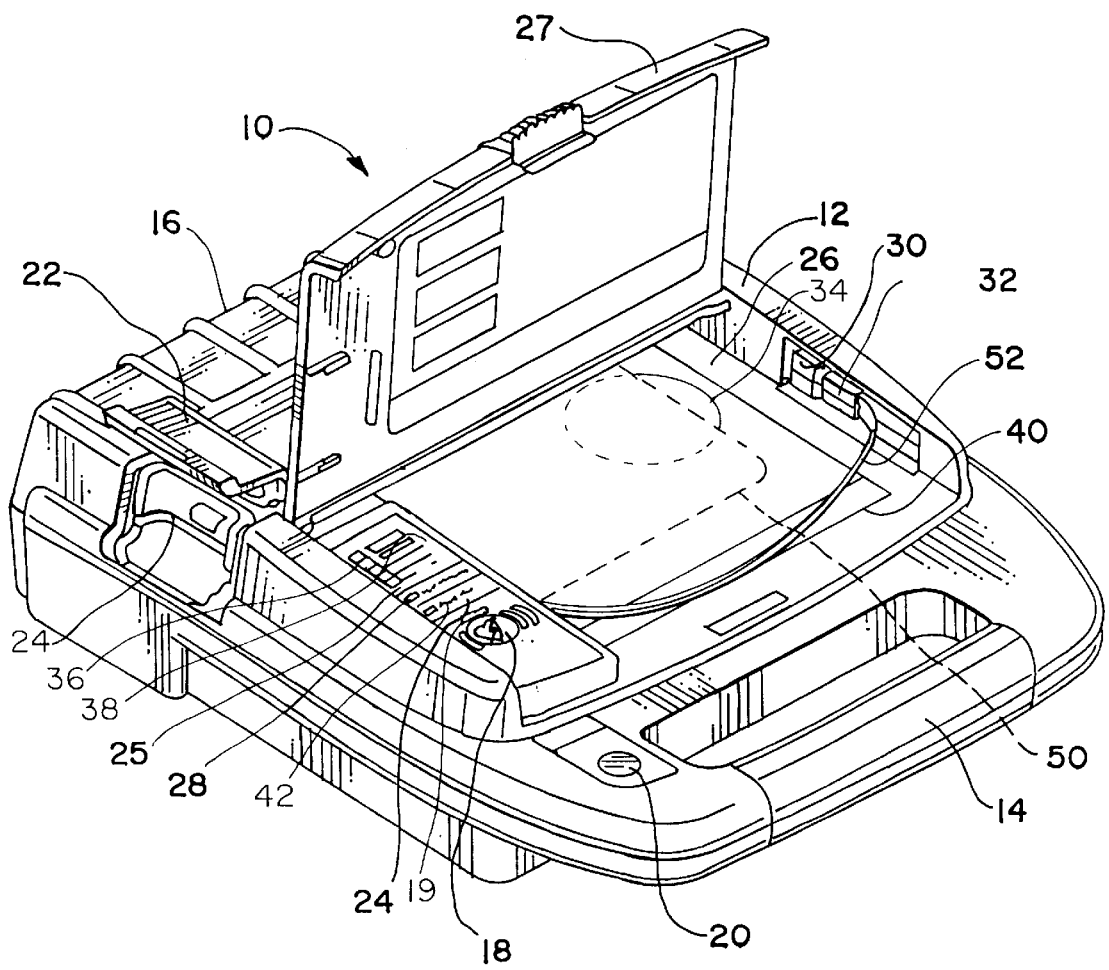
FIG. 1 is a perspective view of an automatic external defibrillator (AED) of the present invention.

The AED of the present invention is shown generally at 10 in FIG. 1. AED 10 includes case 12 with carrying handle 14 and battery pack 16, which is removably disposed within a battery compartment (not shown) in case 12. Battery pack 16 functions as an energy source for AED 10. Visual maintenance indicator 20 and data access door 22 are located on the outside of case 12 to facilitate access by the operator. Case 12 also includes panel 24 and has electrode compartment 26 defined in a top portion thereof. Panel 24 includes illuminable resume/rescue switch 18 and diagnostic display panel 25 with "electrodes" indicator light 28. Panel 24 and electrode compartment 26 are enclosed by selectively closeable lid 27.

Electrode compartment 26 contains electrode connector 30 and electrode pouch 40, which, in the prior art, hermetically encloses an electrode set 50 comprising a pair of electrodes 50A, 50B. Electrodes 50A, 50B are removably connected to electrode connector 30 by leads 52. Connector 30 is typically configured with two connectors, one connector for connecting to a first electrode 50A and the second connector for connecting to a second electrode 50B. Electrodes 50A, 50B are adhered to a patient prior to a rescue intervention procedure with AED 10.

Figure 2A:
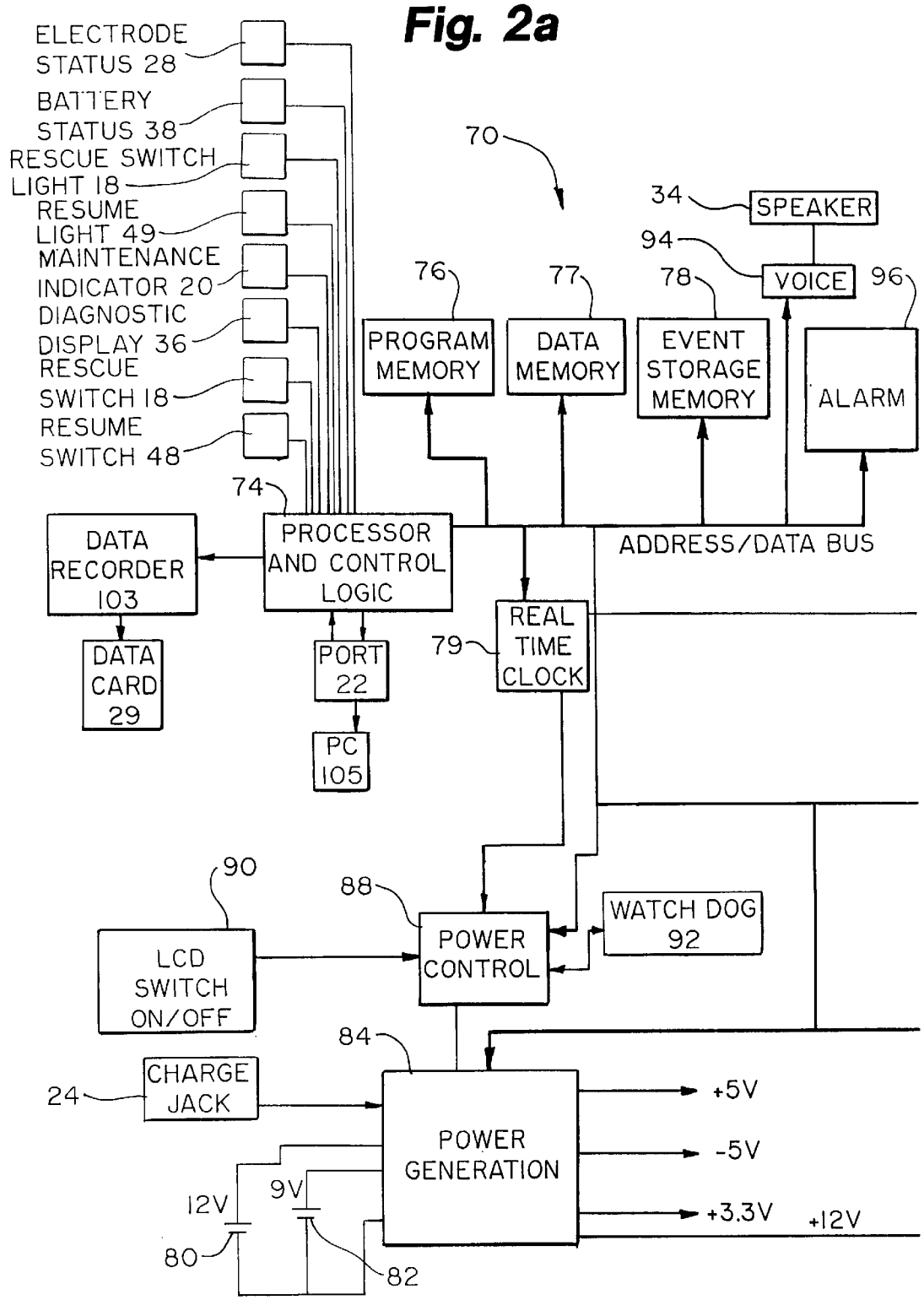
FIG. 2 is schematic of the AED control system.
Figure 2:
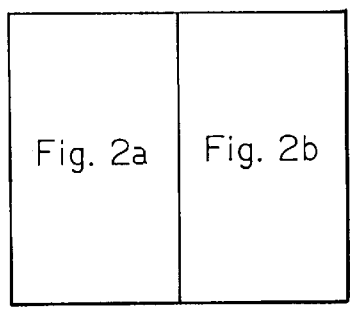
Figure 2B:
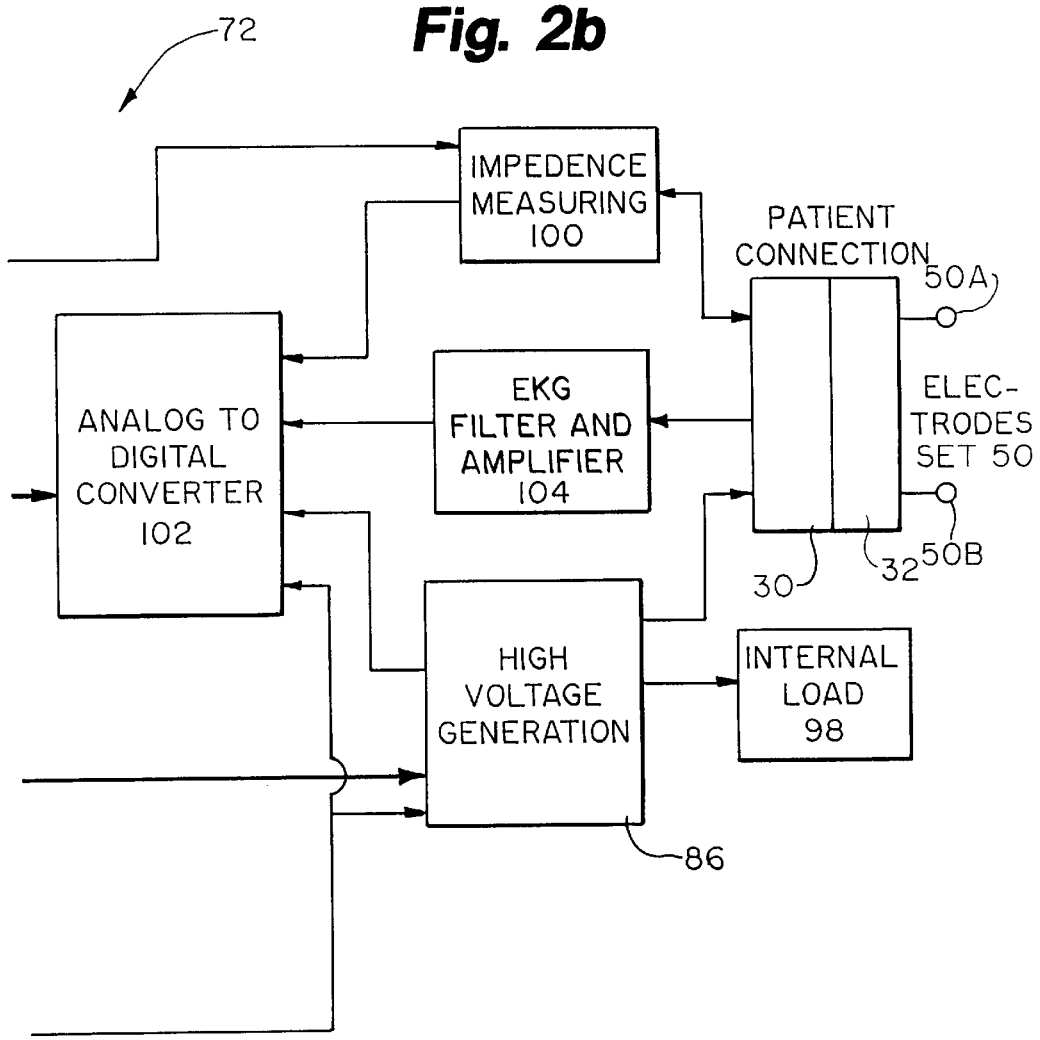

Exemplary electrical system 70 of AED 10 is depicted in the schematic diagram of FIG. 2. The overall operation of AED 10 is controlled by digital microprocessor-based control system 72. Control system 72, in turn, includes processor 74, program memory 76, data memory 77, event memory 78, and real time clock 79. Processor 74 is interfaced to program memory 76, data memory 77, event memory 78 and real time clock 79. The operating program executed by processor 74 is stored in program memory 76. Data memory 77 is used by processor 74 as a scratch pad memory during the execution of an operating program of AED 10.

Electrical power is provided by battery 80 disposed in battery pack 16. In a preferred embodiment, battery 80 is a lithium-sulphur dioxide battery. Battery pack 16 may be removably positioned within the battery compartment of case 12. Battery 80 may include a plurality of interconnected, individual battery cells as desired. Battery 80 is connected to power generation circuit 84. "Battery Status" indicator light 38 (see also FIG. 1) indicates the charge status of battery 80 and prompts the operator to replace battery 80 when necessary.

During normal operation, power generation circuit 84 generates regulated ±5V, and 12V (actually about 5.4V and about 11.6V) supplies with electrical power provided by battery 80. A 3.3V supply is generally used to power real time clock 79 and lid switch 90. The 3.3V supply also powers watch dog timer 92 when lid 27 is in a closed position (e.g., when AED 10 is in a standby mode). The ±5V output of power generation circuit 84 functions as a back-up battery to power components of electrical system 70 during the execution of self-tests (described below). The ±5V output of circuit 84 also activates maintenance indicators and alarms (also described below). Although not separately shown, power generation circuit 84 includes voltage level sensing circuits which are coupled to processor 74. These voltage level sensing circuits provide low battery level signals to processor 74 for display on "Battery Status" indicator light 38.

Power generation circuit 84 is also connected to power control circuit 88 and processor 74. Power control circuit 88 is connected to lid switch 90, watch dog timer 92, real time clock 79 and processor 74. Lid switch 90 is a magnetic reed relay switch in one embodiment or may be a Hall effect sensor. Lid switch 90 provides signals to processor 74 indicating whether lid 27 is open or closed. Serial connector port 23 is coupled to processor 74 for two-way serial data transfer using an RS-232 protocol.

Resume/rescue switch 18, "Maintenance" indicator 20, "Battery Status" indicator light 38, "Electrodes" indicator light 28, and "Service" indicator light 42 of diagnostic display panel 36, voice circuit 94 and piezoelectric audible alarm 96 are also connected to processor 74. Voice circuit 94 is connected to speaker 34. In response to voice prompt control signals from processor 74, voice circuit 94 and speaker 34 generate audible voice prompts provided to the operator.

High voltage generation circuit 86 is also connected to and controlled by processor 74. High voltage generation circuits such as circuit 86 are known and disclosed, for example, in the commonly assigned Persson et al. U.S. Pat. No. 5,405,361, which is hereby incorporated by reference. In response to charge control signals provided by processor 74, high voltage generation circuit 86 is operated in a charge mode. During the charge mode of operation, one set of semiconductor switches (not separately shown) causes a plurality of capacitors (not separately shown) to be charged in parallel to a potential of about 400V. Each capacitor is charged by power supplied by power generation circuit 84. Once charged, and in response to discharge control signals from processor 74, high voltage generation circuit 86 is operated in a discharge mode. During discharge, the capacitors are discharged in series by another set of semiconductor switches (not separately shown) to produce high voltage defibrillation pulses. The defibrillation pulses are applied to the patient by electrodes 50A, 50B of electrode set 50, via electrode connector 32. Electrode connector 32 is connected to high voltage generation circuit 86. Under certain circumstances (described below), processor 74 causes high voltage generation circuit 86 to be discharged through internal resistive load 98 rather than connector 32 to electrode set 50.

Impedance measuring circuit 100 is connected to electrode connector 32 and real time clock 79. Impedance measuring circuit 100 is also interfaced to processor 74 through analog-to-digital (A/D) converter 102. Impedance measuring circuit 100 receives a clock signal with a predetermined magnitude from clock 79 and applies the signal to electrodes 50A, 50B through connector 32. The magnitude of the clock signal received back from electrodes 50A, 50B through connector 32 is monitored by impedance measuring circuit 100. An impedance signal representative of the impedance present across electrode connector 32 is then generated by circuit 100 as a function of the ratio of the magnitudes of the applied and received clock signals (i.e., a measure of the attenuation of the applied signal). For example, if the conductive adhesive on electrodes 50A, 50B is too dry, if electrodes 50A, 50B are not properly connected to connector 32, or if electrodes 50A, 50B are not properly positioned on the patient, a relatively high resistance (e.g., greater than about 200 ohms) will be present across connector 32. The resistance across connector 32 will be between about 25 and 175 ohms when fresh electrodes 50A, 50B are properly positioned on the patient with good electrical contacts. The signal representative of the impedance measured by circuit 100 is digitized by A/D converter 102, then relayed to processor 74.

AED 10 also includes data recorder 103 and electrocardiogram (ECG) filter and amplifier 104. Data recorder 103 is interfaced to processor 74. Data recorder 103 is positioned internally within AED 10 adjacent to data card slot 24 (see also FIG. 1), so as to be ready to accept data (rescue information) card (not shown). ECG filter and amplifier 104 is connected between electrode connector 32 and A/D converter 102. The ECG or cardiac rhythm of the patient is sensed by electrode set 50 when electrodes 50A, 50B are placed on the patient and processed by ECG filter and amplifier 104 in a conventional manner, then digitized by A/D converter 102 before being relayed to processor 74.

The rescue mode of operation of AED 10 is initiated when an operator opens lid 27 to access electrodes 50A, 50B. An opened lid 27 is detected by lid switch 90. Lid switch 90 functions as an on/off switch for AED 10. In response to lid switch 90 being activated when lid 21 is opened, power control circuit 88 activates power generation circuit 84 and initiates the rescue mode operation of processor 74. Processor 74 then begins its rescue mode operation by: (1) switching maintenance indicator 20 to a maintenance required state (a red visual display in one embodiment); (2) flashing the "rescue" light associated with resume/rescue switch 18 and the indicator lights on diagnostic display panel 36; and (3) performing a lid opened self-test.

During the lid opened self-test, checks performed by processor 74 include: (1) the charge state of battery 80; (2) the interconnection and operability of electrodes 50A, 50B (if the electrode test enabled); (3) the state of event memory 78; (4) the functionality of real time clock 79; and (5) the functionality of A/D converter 102. The charge state of battery 80 is checked by monitoring the voltage level signals provided by power generation circuit 84 and comparing these voltage level signals to predetermined nominal values. If battery 80 is determined to have a low charge, the "battery status" indicator 38 on diagnostic display panel 36 will indicate the sensed status. If the electrode self-test is conducted, the interconnection and operability of electrodes 50A, 50B are checked by monitoring the impedance signals provided by impedance measuring circuit 100. If electrodes 50A, 50B are missing or unplugged from connector 32, if electrodes 50A, 50B are damaged, or if the conductive adhesive on electrodes 50A, 50B is too dry, processor 74 will illuminate "Electrodes" indicator light 40 on diagnostic display panel 36.

Also, during the lid opened self-test, processor 74 accesses event memory 78 to determine whether data from a previous rescue operation are still stored therein. If data from a previous rescue are still present, processor 74 causes the "resume" indicator associated with resume/rescue switch 18 on diagnostic panel 36 to be illuminated and initiates the generation of a "Clear Memory" voice prompt. If resume/rescue switch 18 is pressed by the operator following the activation of these indicators, processor 74 clears event memory 78 and proceeds with its rescue mode of operation. The functionality of real time clock 79 and A/D converter 102 are checked by monitoring the outputs of these circuit elements for expected signals. Diagnostic display panel "Service" light 42 is illuminated by processor 74 if faults are identified in real time clock 79 or in A/D converter 102.

If the lid opened self-test is successfully completed, processor 74 switches maintenance indicator 20 to an operational state and initiates the rescue mode of operation of AED 10. In the rescue mode of operation voice circuit 94 generates audible voice prompts through speaker 34 to guide the operator through the operations of AED 10 and, if necessary, delivery of a defibrillation pulse to the patient. AED 10 determines its rescue mode steps of operation by monitoring the impedance across electrode connector 32 and the patient's cardiac rhythm.

Closing lid 27 after rescue mode operation activates processor 74 to initiate and perform a lid closed self-test. During the lid closed self-test, processor 74 performs a comprehensive check of the status and functionality of AED 10 including: (1) the state of event memory 78; (2) the functionality of real time clock 79; (3) the functionality of A/D converter 102; (4) the functionality of program memory 76, data memory 77, and event memory 78; (5) the charge state of battery 80; and (6) the interconnection and operability of electrodes 50A, 50B (if enabled to do so). The state of event memory 78, the state of battery 80, the interconnection and operability of electrodes 50A, 50B, and the functionality of real time clock 79 and A/D converter 102 are checked in a manner identical to that described above with reference to the lid opened self-test.

Conventional memory test routines are also implemented to check the functionality of program memory 76, data memory 77 and event memory 78. Maintenance indicator 20 is switched to its maintenance required state by processor 74 if faults are identified during the lid closed self-test. No audible alarms are actuated if faults are identified in the charge state of battery 80 or the interconnection or functionality of electrodes 50A, 50B during the lid closed self-test.

A daily self-test is also initiated and performed by processor 74 at a predetermined time each day (i.e., every twenty-four hours). During the daily self-test, processor 74 performs all the component check operations described above that are performed during the lid opened and lid closed self-tests. In addition to illuminating the appropriate lights on diagnostic display panel 36, processor 74 leaves maintenance indicator 20 in a maintenance required state if faults are identified during the daily self-test.

Processor 74 also initiates and performs a weekly self-test at a predetermined time one day each week. During the weekly self-test, processor 74 performs all the component check operations described above that are performed during the daily self-test. In addition, processor 74 causes high voltage generation circuit 86 to sequentially operate in its charge and discharge modes, the charge being directed to internal resistive load 98. When high voltage generation circuit 86 is operating in a charge mode, processor 74 monitors the time required to charge the circuit's capacitors and the capacitor voltage. A fault is identified if either time is outside nominal conditions. Maintenance indicator 20 and alarm 96 are actuated in the manner described above if any faults are identified during the weekly self-test. All performed test and patient data may be recorded in event memory 78.

Watch dog timer 92 is set to time watch dog time-out periods of about thirty hours (i.e., a period greater than the twenty-four hour periods between daily self-tests). Watch dog timer 92 is reset by processor 74 at the beginning of each daily self-test and each time lid 27 is opened. In the event control system 70 malfunctions and watch dog timer 92 times out, internal hardware switches maintenance indicator 20 to the maintenance required state and actuates alarm 96 to alert the operator to the fact that AED 10 requires maintenance.

AED 10 facilitates archival storage of rescue information. Data representative of the operation of AED 10 and patient data may be stored in event memory 78 during rescue mode operation. However, if a data card (not shown) is inserted into card slot 24 before the beginning of a rescue attempt, the rescue information is automatically recorded by data recorder 103 onto the data card, thereby also facilitating archival storage of rescue information. Stored data representative of the operation of AED 10 may include the real time of the occurrence of each of the following events: (1)

the placement of electrodes 50A, 50B on the patient, (2) the initiation of the cardiac rhythm analysis voice prompt, (3) the initiation of the charging voice prompt, (4) the completion of the charge mode operation of high voltage generation circuit 86, and (5) the actuation of the resume/rescue switch 18 in the rescue mode. The actual time base of the patient's cardiac rhythm (ECG information) may also be stored. Data representative of the patient may include the monitored cardiac rhythm, key events detected during the rescue operation, and sound occurring within the vicinity of AED 10.

Following a rescue, the stored data may be retrieved from event memory 78 through the use of computer (PC) 105 interfaced to serial connector port 22. Real time clock 79 can also be set through the use of PC 105 interfaced to port 22. If the rescue data were stored on the data card and the data card remains in slot 24, the date may also be retrieved through the use of PC 105 interfaced to serial connector port 22. Alternatively, data card 29 may be removed from slot 24 and inserted into an appropriate card reader (not shown), directly connected to PC 105, such as a PCMCIA type I card reader.

Upon the completion of each lid opened, lid closed, daily and weekly self-test, processor 74 causes a record of the self-test to be stored in event memory 78. Each stored record includes data representative of the date and time of the test and the results of the test. The test results are recorded in the form of a code or other description indicating whether all the functions, components and component status states passed the test, or indicating the nature of any identified faults. In one embodiment, only the records of the twenty most recently performed tests are stored in memory 78. The stored self-test records may be retrieved from memory 78 through PC 105 interfaced to serial connector port 22. Each self-test is powered by the battery 80. The battery 80 may also be coupled to real time clock 79 to continuously provide power thereto.

Selected operating parameters determine how AED 10 administers defibrillation shocks (or pulses), performs self-tests, and stores rescue data. These selected parameters may be modified by an exemplary software-enabled protocol as described below. As indicated in Table 1, these parameters may include "Second Shock Energy", "Maximum Shocks Per Rescue", "Same Energy After Conversion", "Daylight Savings", "Electrode Test", and "External Memory Storage".

TABLE 1

| Function | Default | Selectable Options |
| --- | --- | --- |
| Second Shock Energy (J) | 300J | 200J |
| Maximum Shocks Per Rescue | 255 | 6 to 255 |
| Same Energy After Conversion | Enabled | Disabled |
| Daylight Savings | Enabled | Disabled |
| Electrode Test | Enabled | Disabled |
| External Memory Storage | Long Rescue | Voice Record |

In a rescue intervention, a series of increasing energy level shocks may typically be delivered to a patient. The AED 10 provides for varying the energy of the second shock. The Second Shock Energy parameter determines the energy in Joules (j) delivered in the second defibrillation pulse to a patient by AED 10. The default value for the Second Shock Energy parameter is 300J; however, a value of 200J may be selected.

The Maximum Shocks Per Rescue parameter determines the number of defibrillation pulses delivered by AED 10 during a rescue. The default value for the Maximum Shocks Per Rescue parameter is 255; but, any number of defibrillation pulses between 6 and 255 inclusive may be selected.

The Same Energy After Conversion parameter determines whether the same energy as the previous defibrillation pulse will be delivered when the patient assumes (or converts to) a normal sinus heart rhythm, but then reverts back to a shockable cardiac rhythm. The default status for the Same Energy After Conversion parameter is enabled, e.g., the same energy as the previous pulse will be delivered. This parameter may be disabled by the present protocol as described below.

Figure 3:
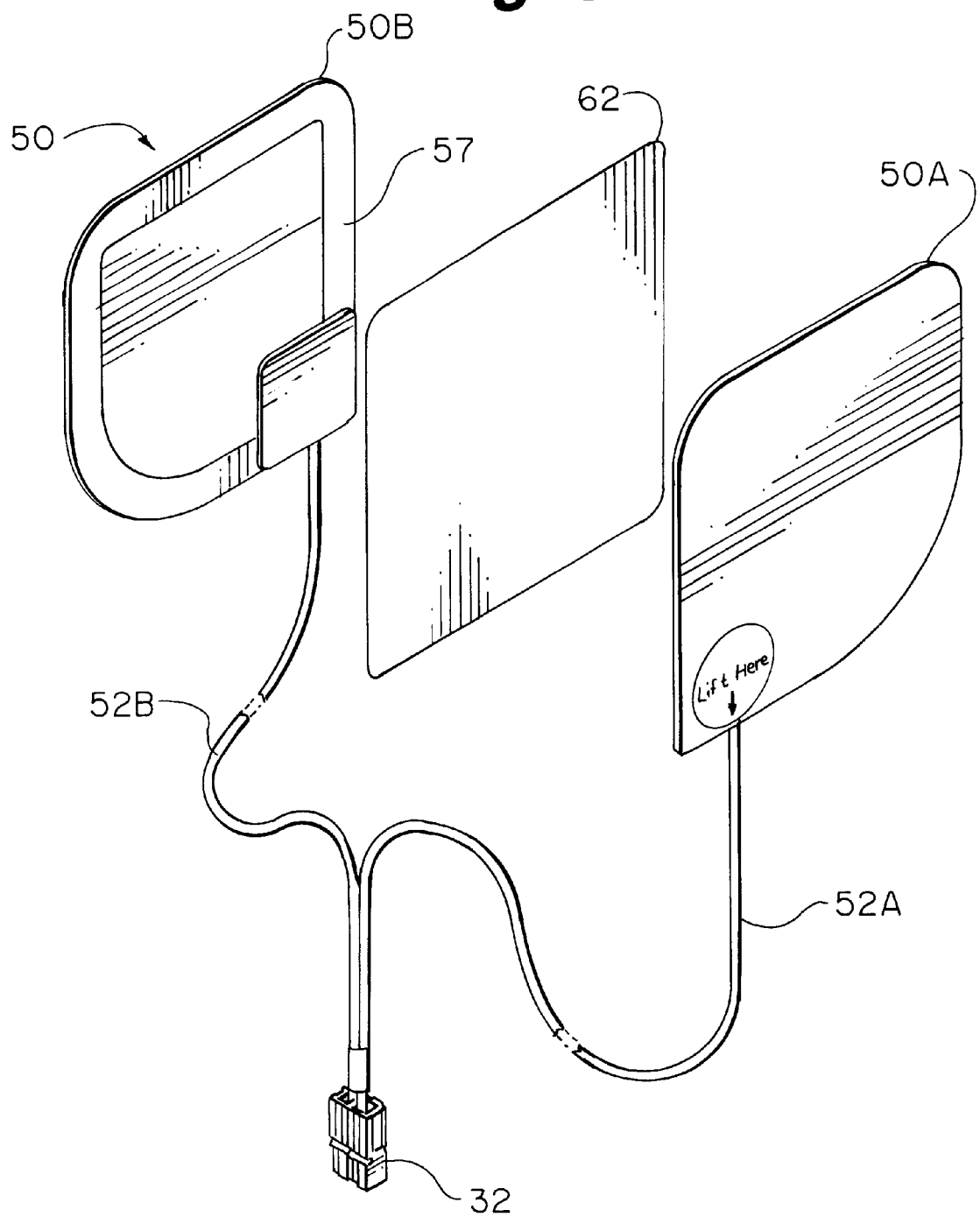
FIG. 3 is an exploded, perspective view of a defibrillation electrode of the present invention.
Figure 4:
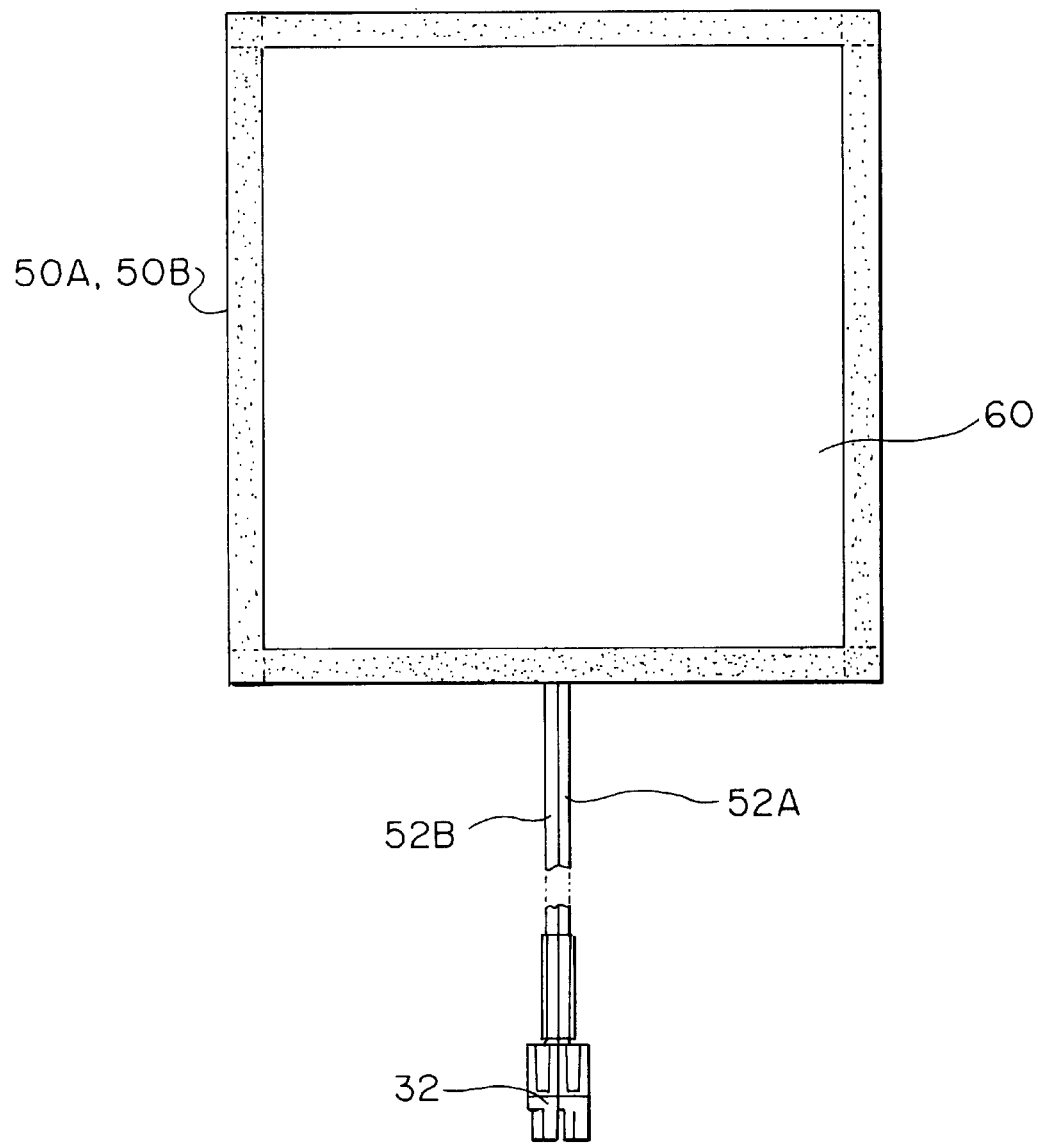
FIG. 4 is a plan view of a package pair of defibrillation electrodes.
Figure 5:
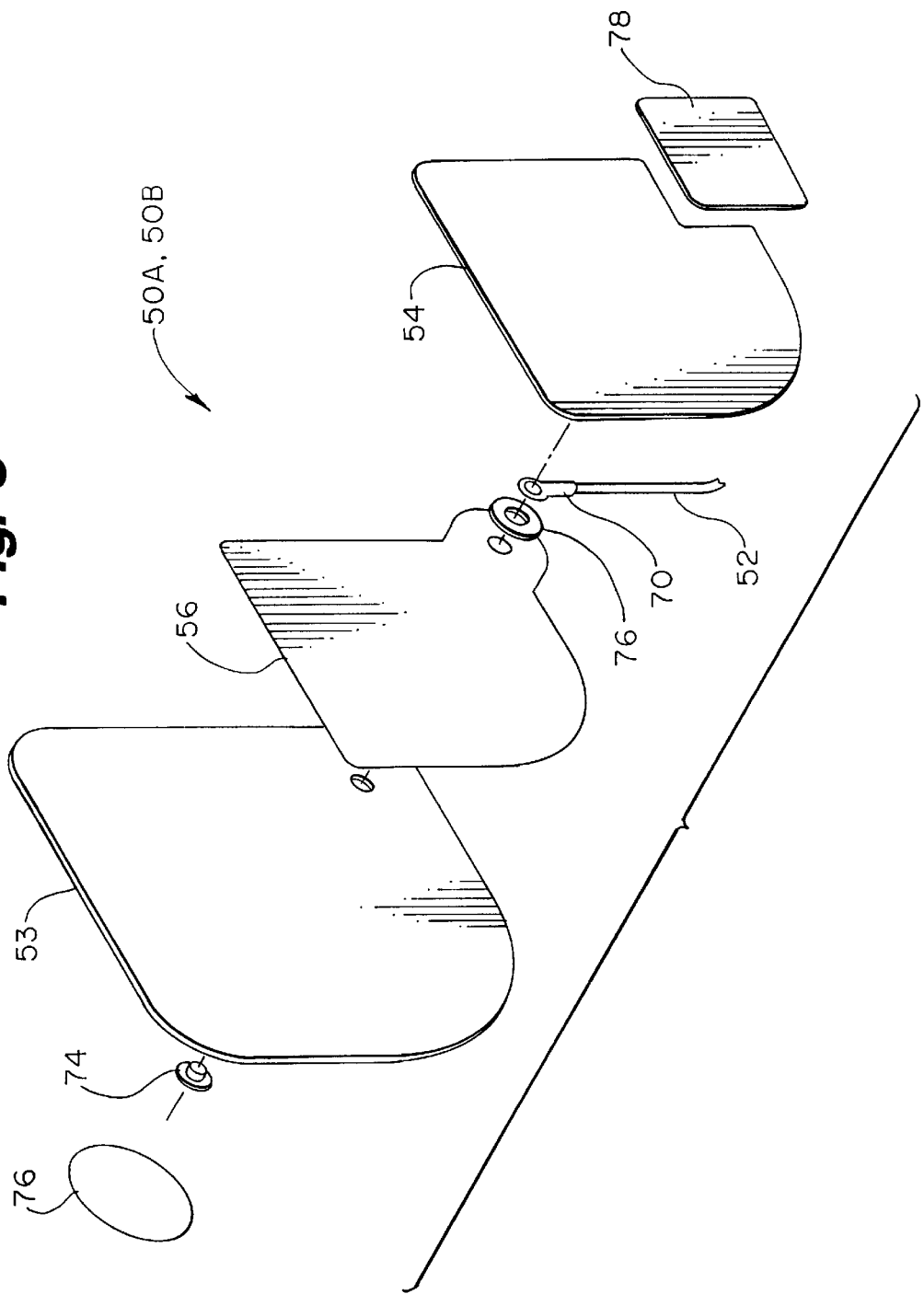
FIG. 5 is an exploded view of a defibrillation electrode.

Referring to FIGS. 3–5, electrodes 50A, 50B include flexible, adhesive coated backing layer 53 (preferably a polymeric foam), and patient engaging layer 54. Patient engaging layer 54 is preferably a hydrogel material which has adhesive properties, and which is electrically conductive. Hydrogel adhesive of this type is commercially available from LecTec Corporation (Minnetonka, Minn.) and Tyco International Ltd. (Hamilton, Bermuda). Current dispersing flexible conductive portion 56 is preferably located between backing layer 53 and patient-engaging hydrogel layer 54. Conductive portion 56, as shown, need not be the same size as backing layer 53 and is preferably a homogeneous, solid, thinly deposited metallic substance, or a conductive ink.

An adhesive coated border 57 is formed by a portion of adhesive coated backing layer 53. This adhesive coated border extends about conductive portion 56 and patient engaging hydrogel layer 54. Insulated lead wire 52 is terminated with a wire terminal 70 at a first end and a connector 32 at a second end. Wire terminal 70 is electrically connected to conductive portion 56 via conductive rivet 74 and washer 72. Conductive rivet 74 is covered on a first side with insulating disk 76. Conductive rivet 74, washer 72, and wire terminal 70 are all covered on a second side with insulating pad 78. Electrode connector 32 is designed to make electrical connection with AED connector 30 (see FIG. 1).

Further examples of electrode pad construction for use with AED 10 are described and shown in U.S. Pat. Nos. 5,697,955, 5,579,919, and 5,402,884, all hereby incorporated by reference.

Figure 6:
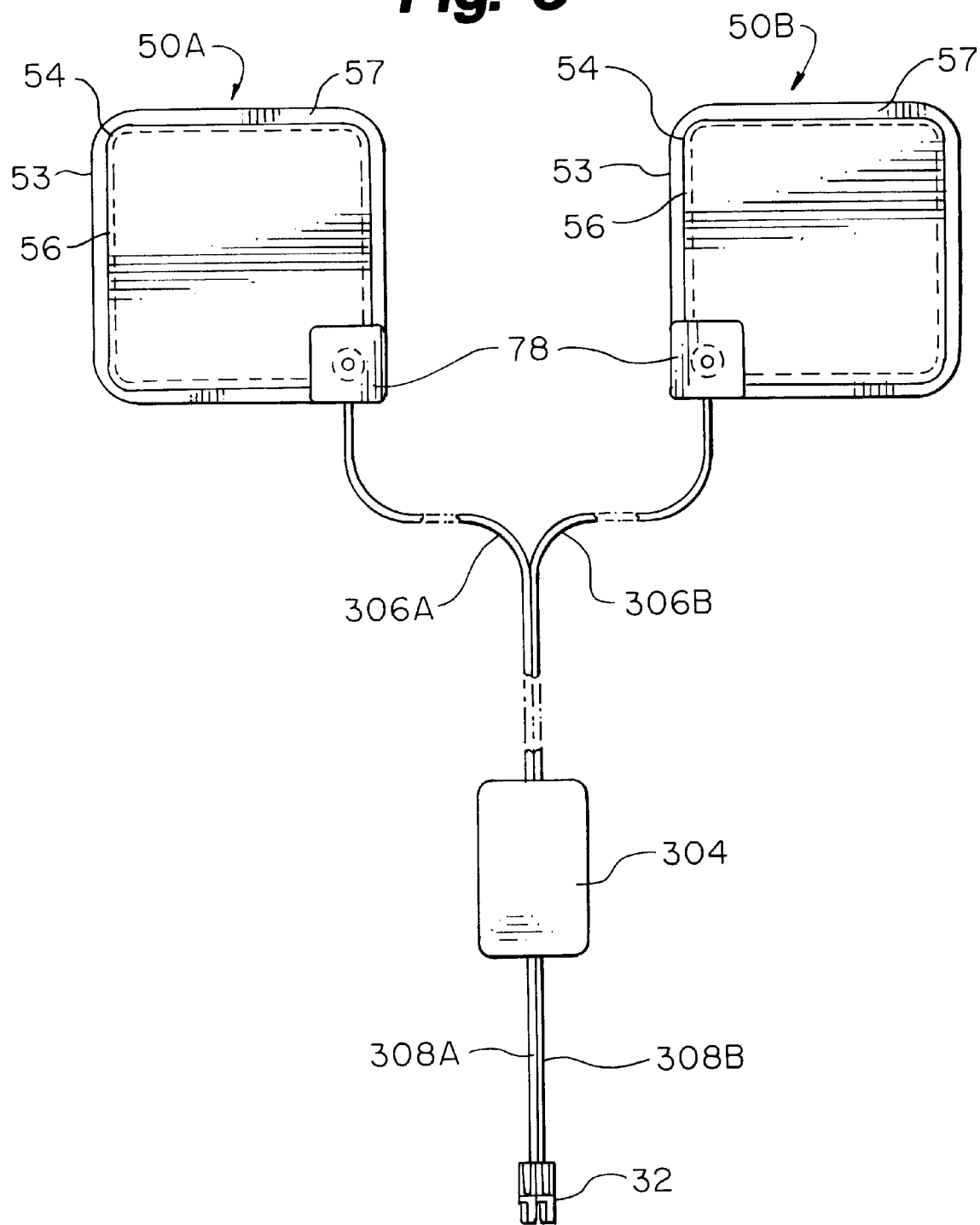
FIG. 6 is a plan view of the defibrillation system of the present invention.

The inventive pediatric electrode set 300 of the present invention is depicted in FIG. 6. Exemplary electrode set 300 includes an electrical connector 320 which mates with AED connector 30 of AED 10.

Electrode set 300 includes a first electrode 50A and a second electrode 50B, substantially as described above with reference to FIGS. 3–5. Electrode set 300 could include more than two electrodes, as desired. Electrodes 50A, 50B include backing layer 53, patient engaging hydrogel layer 54, conductive portion 56, and insulating pad 78. Electrodes 50A, 50B are electrical connected to an energy reducer 304 with lead wires 306A, 306B. Energy reducer 304 is connected to connector 32 with wires 308A, 308B.

FIG. 7 is a block diagram of the pediatric defibrillation set 300 of FIG. 6. Electrodes 50A, 50B are electrically connected to energy reducer 304 by lead wires 306A, 306D. Energy reducer 304 is electrically connected to connector 32 by connecting wires 308A, 308B. Connector 32 is releasably mated with connector 30 of AED 10.

FIG. 8 is a block diagram illustrating a second embodiment of the pediatric defibrillation set 300. Electrodes 50A, 50B are electrically connected to connector 58. Connector 50 is releasably mated with connector 310 of energy reducer 304. Energy reducer 304 is electrically connected to connector 32 by connecting wires 308A, 308B. Connector 32 is releasably mated with connector 30 of AED 10. Those skilled in the art will readily recognize that a number of embodiments are possible for energy reducer 304. These embodiments include networks of electronic components including but not limited to resistors, capacitors, and gas tube surge arrestors.

FIG. 9 is a schematic circuit diagram of one embodiment of the pediatric defibrillation set 300. In this embodiment, energy reducer 304 includes a shunt resistor 320. Resistor 322 represents the electrical impedance between electrodes 50A, 50B when the electrodes 50A, 50B are adhered to the patient. The electrical impedance 322 depicted is the impedance across the patient's chest.

Preferably, the shunt resistor 320 is built into the connecting wires 308A, 308B so that the operator selects a pair of electrodes according to the operator's estimation of the patient's weight. Preferably, four sets of electrodes 50A, 50B are supplied with the AED 10. The electrodes may be color-coded or otherwise identified to correspond to a given patient body weight. The first set of electrodes is adult electrodes 50A, 50B as described with reference to FIGS. 3–5 above, which have no shunt resistor 320 whatsoever. A further three pairs of pediatric electrode systems 300 are supplied with the AED 10. There is preferably one electrode pair for patients who are 0 to 10 kilograms. There is another set of electrodes 50A, 50B, having different identification, that is for patients who are 10 to 20 kilograms in weight. And, there is a pair of electrodes 50A, 50B for patients who are 20 to 40 kilograms. Each of those pediatric electrodes 50A, 50B of pediatric electrode set 300 has a shunt 304 built into the wires 308A, 308B to reduce the energy to the electrodes 50A, 50B.

The first electrode set 300, for the 0 to 10 kilograms body weight, should be about 20 joules delivered to the patient. However, the defibrillators 10 typically escalate the energy level of successive shocks, as indicated above. The adult shocks are typically 200 joules, 300 joules, 360 joules for successive shocks. With the pediatric electrode set 300, the shunt 304 reduces the energy to the electrodes 50A, 50B to about 10 joules, 20 joules, 40 joules. With electrode set 300 adapted for 10 to 20 kilogram patients the reduction would be to about 60 joules, 80 joules, 100 joules. And, with electrode set 300 adapted for patients who are 20 to 40 kilograms the reduction is to around 120 joules, 140 joules and 160 joules.

In a further embodiment as depicted in FIG. 10, an exemplary pediatric electrode set 400 may include special pediatric electrodes 402, 404, which may be a specially reduced sized to better fit a pediatric patient. A number of different sets of electrodes, 402, 404 may be provided, each different set being indicated for use with patients of differing weight ranges. Electrode set 400 may include more than two electrodes, as desired. See electrode 404a, which may be applied to the anterior region of the patient's chest. Electrode set 400 has means of coding AED 10 that can be read by the processor 74 of the AED 10 when the electrode set 400 is plugged into the connector 30 of the AED 10. When the processor 74 detects the special pediatric electrode set 400, the processor 74 changes certain parameters of the detection algorithm to make it more suited to detecting heart rhythms of a pediatric patient by means of the electrodes 402, 404. Further, the processor 74 may select a different set of voice prompts for delivery to speaker 34 that are specifically suited to a pediatric patient for prompting an operator in the delivery of therapy to the pediatric patient. Additionally, the processor 74 may select a pediatric dosage of electricity for the therapeutic shock that is reduced as compared to the above adult dosage.

A further aspect of this invention are means to enable the processor 74 of the AED 10 to detect and identify pediatric electrodes 402, 404. This is alternatively done by resistance or inductance coding, or an imbedded memory chip 408 in the electrodes 402, 404 or other suitable method. In resistance coding, an amount of resistance 405 that is unique to the pediatric set 400 is added to a wire connector 406a, 406b. Resistance 405 may be changed for different electrodes 402, 404 for use with different weight patients. The inductance of the electrode circuit will change with a reduced size of the pediatric electrodes 402, 404 as compared to the larger adult electrodes 50A, 50B. This results from the change in current in the electrode circuit. This change in inductance is detectable by the processor 74 of the AED 10. The inductance will be different for the various electrodes 402, 404 to be used with varying weight pediatric patents. A further benefit of certain types of coding such as inductance coding, is that it allows retrofitting of an existing AED 10 to be converted to this type of pediatric mode with no hardware modifications to the AED 10 by including a software change effected in processor 74 to recognize the coding and to effect the aforementioned changes and by utilization of the specialized pediatric electrodes 402, 404.

Another further aspect of this invention is that the electrodes are further distinguished by the coding to allow for a range of ages of body weights which would allow the processor 74 of AED 10 to fine tune the algorithm and energy dosage to a narrower weight/age range. For example, when an electrode 402 coded to 10–20 lbs. is utilized, AED 10 selects one set of detection and energy specifications for 10–20 lbs., another electrode 402 coded 20–40 lbs. causes AED 10 to select a different set of detection and energy specifications suitable for 20–40 lbs. patients, and still another electrode 402 causes AED 10 to select parameters for 40–60 lbs. patients.

The operation of AED 10 is generally described briefly below. A rescue mode of AED 10 is initiated when lid 27 is opened to access electrodes package 40 containing electrodes 50A, 50B. The opening of lid 27 is detected by lid open on/off switch 90 of the AED 10 to effectively turn on the device. AED 10 then quickly runs a short test routine as indicated above. After electrodes 50A, 50B have been placed on the patient, AED 10 senses patient specific parameters, such as impedance, voltage, current, charge, or other measurable parameters of the patient specifically related to cardiac condition.

If a shockable condition is detected through electrodes 50A, 50B, a plurality of capacitors inside of AED 10 are charged, as indicated above. Based upon the pediatric patient specific parameters sensed, the duration and other characteristics of a discharge waveform are then calculated suitable to a pediatric patient. The energy stored in AED 10 is then discharged to the pediatric patient through electrodes 50A, 50B.

For a more detailed description of the physical structure of AED 10 or the process involved in sensing, charging, shocking, and testing, reference should be made U.S. Pat. No. 5,645,571 entitled AUTOMATED EXTERNAL DEFIBRILLATOR WITH LID ACTIVATED SELF-TEST SYSTEM, which is herein incorporated by reference.

For operation of AED 10 with respect to the present invention, when a first responder arrives at an emergency scene, the responder evaluates the patient's condition and the first responder looks at the patient to estimate the patient's body weight. If the patient is a pediatric patient (less than about 80 lbs.), the responder then picks the appropriate electrode set 300, 400 for a pediatric patient. If the responder determines that the patient is unconscious, not breathing, and has no pulse, the patient is a candidate for therapy delivered by the AED. Connector 32 is releasably mated with connector 30 of AED 10. Electrodes 50A, 50B are then applied to the patient's chest spaced apart to define an electrical path through the patient.

The AED 10 analyzes the rhythm of the patient's heart, preferably using detection parameters suited particularly to a pediatric patient having a selected body weight range, and determines if the patient is in ventricular fibrillation (VF) or another condition which can be treated with a rescue shock. If a shock is advised, the AED 10 will communicate this to the rescuer using voice prompts. The rescuer then pushes rescue button 18 to deliver a shock. A shock having energy appropriate to the specific selected pediatric patient body weight range is delivered to electrodes 50A, 50B.

In the instance when the electrode set 300 is utilized, a normal adult energy level is delivered by AED 10. When the shock is delivered, the energy reducer 304 reduces the energy delivered by AED 10 to the electrodes 50A, 50B to a level appropriate for a pediatric patient. In the embodiment shown in FIG. 8, a portion of the shock energy is delivered to shunt resistor 320, the remainder of the shock energy is delivered to the patient (represented by resistor 322 in FIG. 9). An energy vector is defined preferably centrally through the patient's heart, in order to best effect the defibrillation desired.

In the instance when the electrode set 400 is utilized (FIG. 10), the algorithm of the processor 74 of AED 10 detects the presence of the specific coding associated with the electrode set 400. The voice prompts to the first responder are altered appropriate to the relatively small size of the pediatric patient. Further, the heart rhythm detection parameters are altered appropriate to the relatively small size of the pediatric patient and the shock delivered to the patient is reduced appropriate to the relatively small size of the patient, as indicated by the unique coding of the electrode set 400 for a particular range of body weights.

Although the present invention has been described with reference to preferred embodiments, workers skilled in the art will recognize that changes may be made in form and detail without departing from the spirit or scope of the present invention.

What is claimed is:

1. An automatic external defibrillator (AED) having a case containing a plurality of AED components, including a battery electrically coupled to an AED control system, the control system communicatively coupled to a charge system, the charge system for generating a stored quantity of energy responsive to a communication from the control system, the control system selectively commanding a discharge of the stored energy to an electrical connector, a plurality of removable electrodes in an electrode set, each electrode of the electrode set for making electrical contact with a skin surface of a patient, each electrode being electrically connectable to the AED electrical connector for communicating the stored energy to the patient, the AED comprising:

means for scaling the stored energy communicated to the patient responsive to a known patient weight, wherein each of a two electrodes of the plurality of electrodes has an electrical lead for effecting electrical connection to the AED electrical connector, the means for scaling being an electrical shunt between the two electrodes.

2. The AED of claim 1, wherein at least two of the plurality of electrodes is placeable on the patient spaced apart from each other to define an electrical path through the patient, the path extending between the at least two spaced apart electrodes.

3. The AED of claim 2, wherein the stored energy communicated to the patient generates an energy vector, the energy vector passing through the patient's heart.

4. The AED of claim 1, wherein the electrical shunt is between the two electrode leads.

5. The AED of claim 1, wherein the electrical energy deliverable to the patient is between 10 joules and 160 joules.

6. The AED of claim 5, wherein the electrical energy deliverable to the patient is deliverable in a selectable series of successive shocks, a successive shock increasing in energy level with respect to a preceding shock.

7. The AED of claim 6, wherein the electrical energy deliverable to the patient is deliverable in a selectable series of successive shocks, each successive shock increasing the energy level with respect to the preceding shock, the energy level shocks being selectable as function of a known body weight of the patient and being selected from a list consisting substantially of:

10 joules, 20 joules, 40 joules;
60 joules, 80 joules, 100 joules; and
120 joules, 140 joules, 160 joules.

8. The AED of claim 1, including a plurality of electrode sets.

9. The AED of claim 8, wherein each of the electrode sets is scaled to a known patient body weight.

10. An automatic external defibrillator (AED) having a case containing a plurality of AED components, including a battery electrically coupled to an AED control system, the control system communicatively coupled to a charge system, the charge system for generating a stored quantity of energy responsive to a communication from the control system, the control system selectively commanding a discharge of the stored energy to an electrical connector, a plurality of removable electrodes in an electrode set, each electrode of the electrode set for making electrical contact with a skin surface of a patient, each electrode being electrically connectable to the AED electrical connector for communicating the stored energy to the patient, the AED comprising:

means for scaling the stored energy communicated to the patient responsive to a known patient weight, wherein the means for scaling are coding means operably coupled to the plurality of electrode sets, each electrode set having coding means related to a known range of body weights of the patient.

11. The AED of claim 9, wherein the coding means are recognizable at the AED electrical connector.

12. The AED of claim 10, wherein the coding means are recognizable by the AED control system, the AED control system selectively commanding a reduced discharge of the stored energy to the electrical connector and to the electrode set responsive to the recognized coding means.

13. The AED of claim 11, wherein the coding means are selected from a list consisting of:

resistance coding;
inductance coding; and
an imbedded memory chip coding.

14. The AED of claim 9 wherein the coding means are selected from a list consisting of:

resistance coding, inductance coding, an imbedded chip coding.

15. The AED of claim 14 wherein the resistance coding is a selected amount of resistance added to a specific electrode set, the selected amount of resistance bearing a known relationship to a patient weight range.

16. The AED of claim 15 wherein the inductance coding is inherent to a specific electrode set, the size of the electrodes of the electrode set bearing a known relationship to a patient weight range.

17. The AED of claim 16 wherein the inductance coding is related to the current in a specific electrode set, the size of the electrodes of the electrode set bearing a known relationship to a patient weight range and affecting the current in the specific electrode set.

18. The AED of claim 17 wherein the coding means are detectable by control system software.

19. An electrode set, for use with an automatic external defibrillator (AED), the AED having a case containing a plurality of AED components, including a battery electrically coupled to an AED control system, the control system communicatively coupled to a charge system, the charge system for generating a stored quantity of energy responsive to a communication from the AED control system, the AED control system selectively commanding a discharge of the stored energy to an AED electrical connector, the electrode set comprising:

a plurality of electrodes for making electrical contact with a skin surface of a patient and each electrode of the plurality of electrodes being electrically connectable to the AED electrical connector for communicating the stored energy to the patient; and means for scaling the stored energy communicated to the patient responsive to a known patient body weight, the means for scaling being an electrical shunt between the two electrodes.

20. The electrode set of claim 13, wherein at least two of the plurality of electrodes is placeable on the patient spaced apart from each other to define an electrical path through the patient, the path extending between the at least two spaced apart electrodes.

21. The electrode set of claim 14, wherein the stored energy communicated to the patient generates an energy vector, the energy vector passing substantially through the patient's heart.

22. The electrode set of claim 13, wherein the electrical shunt is between the two electrode leads.

23. The electrode set of claim 17, wherein the electrical shunt is selected from a list consisting of:

resistive means;

capacitive means; and gas tube surge arrestor means.

24. A method of defibrillating the heart of a human patient using an AED, the AED having electrical energy discharge circuitry for generating a dischargeable defibrillating energy to affect the heart of the patient, the heart being in a state of abnormal rhythm, comprising the steps of:

adherably placing at least two electrodes on a skin surface of the patient, the electrodes being spaced apart to define a desired energy path therebetween;

scaling the dischargeable defibrillating energy responsive to a known patient body weight;

discharging defibrillating energy across the energy path, the discharge generating an energy vector, the vector being passable through the heart of the patient; and providing a plurality of different electrode sets with the AED, each electrode set being indicated for use with a selected and different patient body weight.

25. The method of claim 19, further including the step of coding each of the plurality of different electrode packages, the coding being recognizable by an AED control system.

26. The method of claim 21, further including the step of scaling the energy output of the AED electrical discharge circuitry responsive to the coding recognizable by the AED control system.

27. The method of claim 22, further including the step of scaling the energy output of the AED electrical discharge circuitry responsive to the coding recognizable by the AED control system by selecting an energy discharge from a list consisting substantially of:

successive discharges of 10 joules, 20 joules, 40 joules;

successive discharges of 60 joules, 80 joules, 100 joules; and successive discharges of 120 joules, 140 joules, 160 joules.

28. The method of claim 19, further including the step of providing a shunt between the at least two electrodes.

29. The method of claim 24, further including the step of scaling the energy output of the AED electrical discharge circuitry by means of the shunt, the shunt acting to shunt a desired portion of an energy output of the AED electrical discharge circuitry from the at least two electrodes.

30. The method of claim 25, further including the step of scaling the energy output of the AED electrical discharge circuitry by providing a shunt for effecting an energy discharge across the at least two electrodes, the resulting energy discharge across the at least two electrodes for successive discharges being selected from a list consisting substantially of:

10 joules, 20 joules, 40 joules;

60 joules, 80 joules, 100 joules; and 120 joules, 140 joules, 160 joules.

31. The method of claim 19, further including the step of sensing the cardiac rhythm of the patient's heart.

32. The method of claim 27, wherein the sensing parameters are scaled to a pediatric patient.

33. The method of claim 28, further including the step of analyzing the cardiac rhythm to determine whether to deliver a discharge of electrical energy to the patient's heart.

34. The method of claim 31, further including the step of providing an audible voice prompt when a discharge of electrical energy to the patient's heart is warranted.

35. The method of claim 19, further including the step of performing a self-test on the electrodes.

36. The method of claim 29, wherein the self-test step is effected by applying an electrical current between at least two of the plurality of electrodes.

* * * * *